United States Patent
Zhang et al.

(10) Patent No.: US 12,304,906 B2
(45) Date of Patent: May 20, 2025

(54) METHOD FOR PREPARING LURASIDONE HYDROCHLORIDE

(71) Applicants: ZHEJIANG HUAHAI PHARMACEUTICAL CO., LTD., Zhejiang (CN); SHANGHAI SYNCORES TECHNOLOGIES INC. LTD., Shanghai (CN)

(72) Inventors: Yikai Zhang, Shanghai (CN); Junzheng Huang, Shanghai (CN); Hao Lu, Shanghai (CN); Xiaowen Guo, Shanghai (CN); Yafei Jiang, Shanghai (CN); Yuanhai Gao, Shanghai (CN); Luning Huang, Shanghai (CN); Anping Tao, Shanghai (CN); Jianguo An, Shanghai (CN); Hong Gu, Shanghai (CN)

(73) Assignees: Zhejiang Huahai Pharmaceutical Co., Ltd., Zhejiang (CN); Shanghai Syncores Technologies Inc. Ltd., Shanghai (CN)

( * ) Notice: Subject to any disclaimer, the term of this patent is extended or adjusted under 35 U.S.C. 154(b) by 528 days.

(21) Appl. No.: 17/787,369

(22) PCT Filed: Dec. 7, 2020

(86) PCT No.: PCT/CN2020/134285
§ 371 (c)(1),
(2) Date: Jun. 20, 2022

(87) PCT Pub. No.: WO2021/129364
PCT Pub. Date: Jul. 1, 2021

(65) Prior Publication Data
US 2023/0037151 A1   Feb. 2, 2023

(30) Foreign Application Priority Data

Dec. 24, 2019 (CN) .......................... 201911346683.5

(51) Int. Cl.
C07D 417/08   (2006.01)
C07D 417/12   (2006.01)

(52) U.S. Cl.
CPC .................................. *C07D 417/08* (2013.01)

(58) Field of Classification Search
CPC ........................... C07D 417/08; C07D 417/12
See application file for complete search history.

(56) References Cited

FOREIGN PATENT DOCUMENTS

| | | |
|---|---|---|
| CN | 1832946 A | 9/2006 |
| CN | 104031041 A | 9/2014 |
| CN | 106397424 A | 2/2017 |
| CN | 106518729 A | 3/2017 |
| CN | 106916151 A | 7/2017 |
| CN | 109705112 A | 5/2019 |
| CN | 110114063 A | 8/2019 |
| EP | 0464846 A1 | 1/1992 |
| WO | 2012123858 A1 | 9/2012 |
| WO | 2013132511 A1 | 9/2013 |
| WO | 2017154021 A1 | 9/2017 |

OTHER PUBLICATIONS

International Search Report and Written Opinion dated Mar. 9, 2021 in corresponding International Application No. PCT/CN2020/134285 filed Dec. 7, 2020 (6 pages) with Google machine translation (4 pages).
First Office Action dated Nov. 23, 2023 in related Chinese Application No. 202080081396.0 filed Dec. 7, 2020 (7 pages) with CNIPA machine translation (5 pages).

*Primary Examiner* — Brenda L Coleman
(74) *Attorney, Agent, or Firm* — Daniel F. Nesbitt; Nesbitt IP LLC

(57) ABSTRACT

A method for preparing lurasidone hydrochloride by reacting lurasidone free alkali reacts with hydrochloric acid in a mixed solvent of an alcoholic solvent and an alkyl halide solvent.

12 Claims, No Drawings

METHOD FOR PREPARING LURASIDONE HYDROCHLORIDE

The present application is a national phase entry of International Application No. PCT/CN2020/134285 filed on Dec. 7, 2020, which claims the benefit of priority of Chinese patent application No. 201911346683.5, titled "Method of preparing lurasidone hydrochloride", filed on Dec. 24, 2019 before China Patent Office, which are hereby incorporated by reference in their entireties.

TECHNICAL FIELD

The invention belongs to the technical field of medicinal chemistry, and in particular relates to a method for preparing a hydrochloride of lurasidone free base.

BACKGROUND

Lurasidone hydrochloride, jointly developed by Dainippon Sumitomo and Sunovion Inc., US, is a dopamine and serotonin receptor inhibitor for the treatment of schizophrenia and bipolar disorder. Lurasidone hydrochloride is expected to have higher efficacy and safety due to its ability to reduce extrapyramidal reaction and cardiac side effects, and to control weight gain. United States Food and Drug Administration (FDA) approved its listing under the trade name Latuda for the treatment of schizophrenia on Oct. 28, 2010. It has also been approved in Canada.

Lurasidone hydrochloride is an atypical antipsychotic, and its exact mechanism in the treatment of schizophrenia, like other atypical antipsychotics, is still unclear, and may be related to the antagonism between dopamine D2 and serotonin 2A (5-HT2A) receptors. Studies have reported that lurasidone hydrochloride can improve cognitive function when used in the treatment of schizophrenia. Lurasidone hydrochloride, with chemical name of (3aR,4S,7R,7aS)-2-[(1R,2R)-2-[4-(1,2-benzisothiazol-3-yl)piperazine-1-ylmethyl]cyclohexylmethyl]hexahydro-1H-4,7-methylisoindole-1,3-dione hydrochloride. The structure is shown in formula (I):

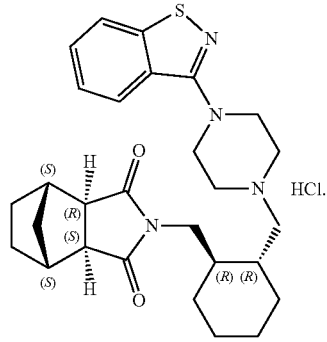

(I)

According to patent publication EP0464846A1, lurasidone hydrochloride (compound of formula I) can be formed into a salt by reacting hydrogen chloride isopropanol solution and lurasidone free base, and the crystallization yield of this method is low. In addition, according to the data reported by the original research patent publication CN1832946A, it is necessary to process an acetone solution of lurasidone with 1.8~5.0% hydrochloric acid to obtain lurasidone hydrochloride (compound of formula I) with acetone-soluble residue <5000 ppm. The yield of this process is only about 85%. When using hydrochloric acid with a concentration of more than 5.0%, the acetone solvent residue in the obtained final product lurasidone hydrochloride is more than 5000 ppm. According to the ICH Guidelines on Residual Solvents in Drugs (ICH Q3C), acetone belongs to the third class of solvents, of which limit in a product is ≤5000 ppm. Furthermore, according to the description in CN1832946A, when using the hydrochloric acid with a concentration of 1.8% to carry out the salt-forming reaction, the yield of the obtained compound is only 65%, and a large amount of product is lost in the mother liquor. It follows that when the above process is applied to large-scale production, the production cost will increase.

In addition, people tried to form salts in alcoholic solvents, but found that lurasidone free base was insoluble in alcoholic solvents. Under reflux conditions, it needed an alcoholic solvent of 20 times more than the mass of the free base for complete dissolving, so that large-scale production is greatly limited.

SUMMARY

The technical problem to be solved by the present application is to provide an economical, safe and effective salt-forming method for lurasidone, which can avoid the residual solvent exceeding the standard of the product.

The application provides a method for preparing lurasidone, comprising: heating and dissolving lurasidone free base (compound of formula II) in a mixed solvent of alcoholic solvent and dichloromethane, adding hydrochloric acid solution to carry out a salt-forming reaction; cooling, crystallizing, and drying to obtain lurasidone hydrochloride. The reaction scheme is as follows:

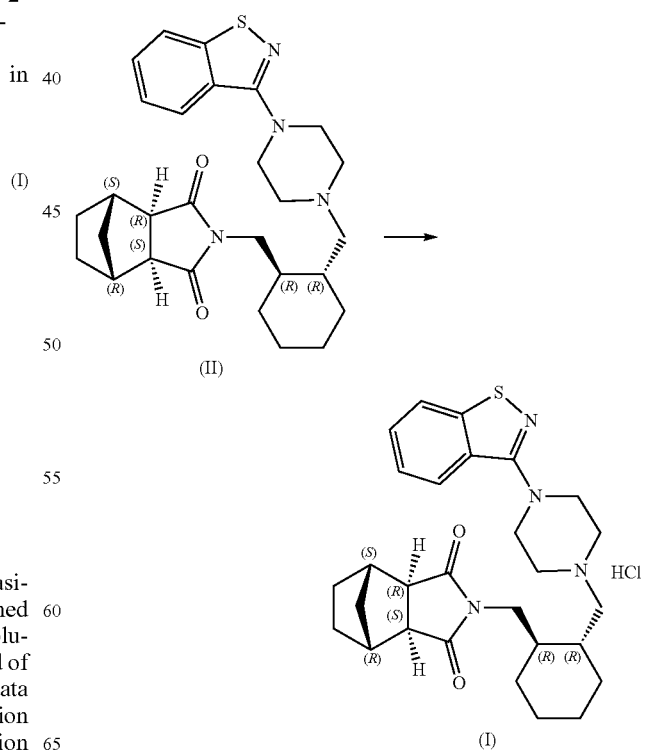

The alcoholic solvent according to the present application can be one or more of methanol, ethanol, isopropanol, n-propanol, n-butanol, sec-butanol, isobutanol, ethylene glycol, 1,2-propanediol, 1,3-propanediol, 1,4-butanediol, 2,3-butanediol, 1,5-pentanediol, 1,6-hexanediol and glycerol; preferably methanol, ethanol or isopropanol.

In the present application, the molar ratio of hydrogen chloride in the hydrochloric acid solution to lurasidone free base is 20:1 to 1:1, preferably 10:1 to 1:1.

In the present application, the hydrochloric acid solution used is aqueous hydrogen chloride solution, or a solution formed by mixing an aqueous hydrogen chloride solution with an appropriate amount of the alcoholic solvent. The hydrochloric acid concentration number (the mass ratio of hydrogen chloride to solution, expressed as a percentage w/w %) concentration can be 0.3% to saturated concentration; preferably 15% to 38% (w/w).

In the present application, the mass-to-volume ratio of lurasidone free base to the alcoholic solvent is 1:5 to 1:50 (W/V); preferably 1:8 to 1:20 (W/V).

In the present application, the mass-to-volume ratio of lurasidone free base to dichloromethane is 1:0.5 to 1:10 (W/V); preferably 1:1 to 1:4 (W/V).

In the present application, the method of adding hydrochloric acid is not particularly limited. For example, it can be added quickly at one time, or it can be diluted with the solvent used and added dropwise. The time for dropwise addition can be either 1 minute or 10 hours.

The crystallization and the filtration operations described in the present application are not particularly limited. Conventional crystallization methods in the art, such as standing cooling or stirring cooling, are used. Filtration can be conventional pressure filtration or centrifugal filtration. Before filtration, the temperature of the crystallization feed liquid is usually −20 to 50° C., preferably 0 to 10° C.

In the present application, the drying method is not particularly limited, and can be drying under reduced pressure, drying under normal pressure, airflow drying, or the like. The drying temperature is 0° C. to 120° C., preferably 35° C. to 65° C.

In the instance that does not violate the common knowledge in the art, the above-mentioned conditions can be arranged and combined in any order, that is, the following embodiments of the present application can be obtained.

The lurasidone hydrochloride (compound of formula I) prepared according to the method of the present application meets the requirements of conventional quality standards, especially the requirements of ICH on residual solvents in medicines. In addition, according to the method of the present application, the yield of lurasidone hydrochloride reaches 95% and more than 95%. In addition, compared with the prior art that uses isopropanol as a single solvent, the amount of solvent used in the method of the present application is greatly reduced, which can not only reduce costs, simplify post-processing, but also improve the stability and reliability of the process, and provide a guarantee for industrial scale production.

DETAILED DESCRIPTION

The present application is further described below by way of examples. Obviously, the described examples are only a part of, but not all, examples of the present application. Based on the examples of the present application, all other examples obtained by those skilled in the art without creative efforts shall fall within the protection scope of the present application.

The raw materials or reagents used in the examples are commercially available unless otherwise specified.

Example 1

10 g of lurasidone free base (compound II) was added to a mixed system of 80 mL of ethanol and 20 mL of dichloromethane, and then the system was heated to dissolved at reflux. After that, the premixed hydrochloric acid ethanol solution (2.26 g 36% concentrated hydrochloric acid+20 mL ethanol) was added dropwise under reflux. After the dropwise addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 10.5 g lurasidone hydrochloride (compound I), yield 98%, ethanol residue: 11 ppm, dichloromethane residue: 39 ppm.

Example 2

10 g of lurasidone free base (compound II) was added to a mixed system of 90 mL of ethanol and 20 mL of dichloromethane, and then the system was heated to dissolved at reflux. After that, the premixed hydrochloric acid ethanol solution (6.17 g 36% concentrated hydrochloric acid+10 mL ethanol) was added dropwise under reflux. After the dropwise addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 10.5 g lurasidone hydrochloride (compound I), yield 98%, ethanol residue: 6 ppm, dichloromethane residue: 43 ppm.

Example 3

50 g of lurasidone free base (compound II) was added to a mixed system of 500 mL of ethanol and 50 mL of dichloromethane, and then the system was heated to dissolved at reflux. After that, 11.31 g 36% concentrated hydrochloric acid was added under reflux. After the addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 51.53 g lurasidone hydrochloride (compound I), yield 96%, ethanol residue: 19 ppm, dichloromethane residue: 6 ppm.

Example 4

10 g of lurasidone free base (compound II) was added to a mixed system of 100 mL of isopropanol and 20 mL of dichloromethane, and then the system was heated to dissolved at reflux. After that, 20.56 g 36% concentrated hydrochloric acid was added under reflux. After the addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C.

to 50° C. to obtain 10.2 g lurasidone hydrochloride (compound I), yield 95%, isopropanol residue: 22 ppm, dichloromethane residue: 82 ppm.

Example 5

10 g of lurasidone free base (compound II) was added to a mixed system of 70 mL of ethanol and 20 mL of dichloromethane, and then the system was heated to dissolved at reflux. After that, the premixed hydrochloric acid ethanol solution (5.43 g 15% concentrated hydrochloric acid+10 mL ethanol) was added dropwise under reflux. After the dropwise addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 10.3 g lurasidone hydrochloride (compound I), yield 96%, ethanol residue: 36 ppm, dichloromethane residue: 31 ppm.

Example 6

10 g of lurasidone free base (compound II) was added to a mixed system of 80 mL of methanol and 40 mL of dichloromethane, and then the system was heated to dissolved at reflux. After that, the premixed hydrochloric acid methanol solution (2.06 g 36% concentrated hydrochloric acid+20 mL methanol) was added dropwise under reflux. After the dropwise addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 10.0 g lurasidone hydrochloride (compound I), yield 93%, methanol residue: 20 ppm, dichloromethane residue: 63 ppm.

Example 7

10 g of lurasidone free base (compound II) was added to a mixed system of 100 mL of ethanol and 20 mL of dichloromethane, and then the system was heated to dissolved at reflux. After that, the premixed hydrochloric acid ethanol solution (3.26 g 36% concentrated hydrochloric acid+50 mL ethanol) was added dropwise under reflux. After the dropwise addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 10.7 g lurasidone hydrochloride (compound I), yield 100%, ethanol residue: 50 ppm, dichloromethane residue: 36 ppm.

Example 8

20 kg of lurasidone free base (compound II) was added to a mixed system of 80 L of ethanol and 20 L of dichloromethane, and then the system was heated to dissolved at reflux. After that, the premixed hydrochloric acid ethanol solution (2.26 kg 36% concentrated hydrochloric acid+20 mL ethanol) was added dropwise under reflux. After the dropwise addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 21.1 kg lurasidone hydrochloride (compound I), yield 98%, ethanol residue: 86 ppm, dichloromethane residue: 60 ppm.

TABLE 1

Summary of experimental parameters and experimental results of Examples 1 to 8

| Examples | Alcoholic solvent | Haloalkane Co-solvent | The mass-to-volume ratio of compound II to alcoholic solvent (g/mL) | The mass-to-volume ratio of compound II to haloalkane (g/mL) | Molar equivalent of hydrogen chloride | Hydrochloric acid concentration (%) | Yield (%) | Alcoholic solvent residue (ppm) | Haloalkane residue (ppm) |
|---|---|---|---|---|---|---|---|---|---|
| 1 | Ethanol | Dichloromethane | 1:10 | 1:2 | 1.1 | 36 | 98 | 11 | 39 |
| 2 | Ethanol | Dichloromethane | 1:10 | 1:2 | 3.0 | 36 | 98 | 6 | 43 |
| 3 | Ethanol | Dichloromethane | 1:10 | 1:1 | 1.1 | 36 | 96 | 19 | 6 |
| 4 | Isopropanol | Dichloromethane | 1:10 | 1:2 | 10.0 | 36 | 95 | 22 | 82 |
| 5 | Ethanol | Dichloromethane | 1:8 | 1:2 | 1.1 | 15 | 96 | 36 | 31 |
| 6 | Methanol | Dichloromethane | 1:10 | 1:4 | 1.0 | 36 | 93 | 20 | 63 |
| 7 | Ethanol | Dichloromethane | 1:15 | 1:2 | 1.1 | 25 | 100 | 50 | 36 |
| 8 | Ethanol | Dichloromethane | 1:10 | 1:2 | 1.1 | 36 | 98 | 86 | 60 |

Comparative Example 1

10 g of lurasidone free base (compound II) was added to 150 mL of acetone, and then the system was heated to dissolved at reflux. After that, the 2.26 g 36% concentrated hydrochloric acid was added dropwise under reflux. After the dropwise addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 10.5 g lurasidone hydrochloride (compound I), yield 98%, acetone residue: 24300 ppm (unqualified).

Comparative Example 2

10 g of lurasidone free base (compound II) was added to 150 mL of acetone, and then the system was heated to dissolved at reflux. After that, 4.43 g 15% concentrated hydrochloric acid was added dropwise under reflux. After the dropwise addition, the system was stirred under reflux for 1 h to 2 h, until it became turbid. Cooling was started, and the system was slowly cooled down to 0° C. to 10° C.

within 2 h to 3 h, and stirred at 0° C. to 10° C. for 1 h to 2 h. The resultant was filtered, and the filter cake was dried under vacuum at 45° C. to 50° C. to obtain 10.5 g lurasidone hydrochloride (compound I), yield 98%, acetone residue: 16800 ppm (unqualified).

Comparative Example 3

10 g of lurasidone free base (compound II) was added to 150 mL of acetone, and then the system was heated to dissolved at reflux. After that, 22.6 g 3.6% concentrated hydrochloric acid was added dropwise under reflux. After the dropwise addition, the system was stirred under reflux for 1 h to 2 h, until it became turbid. Cooling was started, and the system was slowly cooled down to 0° C. to 10° C. within 2 h to 3 h, and stirred at 0° C. to 10° C. for 1 h to 2 h. The resultant was filtered, and the filter cake was dried under vacuum at 45° C. to 50° C. to obtain 7.6 g lurasidone hydrochloride (compound I), yield 71% (low yield), acetone residue: 750 ppm.

The above are only preferred examples of the present application, and are not intended to limit the present application. Any modifications, equivalent replacements, improvements, etc. made within the spirit and principles of the present application should be included within the protection scope of the present application.

The invention claimed is:

1. A method for preparing lurasidone hydrochloride, comprising:
heating and dissolving lurasidone free base in a mixed solvent of alcoholic solvent and dichloromethane, adding hydrochloric acid solution to carry out a salt-forming reaction; and
cooling, crystallizing, filtering and drying to obtain lurasidone hydrochloride.

2. The method according to claim 1, wherein the alcoholic solvent is one or more of methanol, ethanol, isopropanol, n-propanol, n-butanol, sec-butanol, isobutanol, ethylene glycol, 1,2-propanediol, 1,3-propanediol, 1,4-butanediol, 2,3-butanediol, 1,5-pentanediol, 1,6-hexanediol and glycerol.

3. The method according to claim 2, wherein the alcoholic solvent is selected from the group consisting of methanol, ethanol, and isopropanol.

4. The method according to claim 1, wherein the concentration of the hydrochloric acid solution is from 0.3% (w/w) to saturated concentration.

5. The method according to claim 4, wherein the concentration of the hydrochloric acid solution is 15% to 38% (w/w).

6. The method according to claim 1, wherein the molar ratio of hydrogen chloride in the hydrochloric acid solution to lurasidone free base is 20:1 to 1:1.

7. The method according to claim 6, wherein the molar ratio of hydrogen chloride in the hydrochloric acid solution to lurasidone free base is 10:1 to 1:1.

8. The method according to claim 1, wherein the hydrochloric acid solution is an aqueous hydrochloric acid solution, or a solution formed by mixing an aqueous hydrochloric acid solution with an appropriate amount of the alcoholic solvent.

9. The method according to claim 1, wherein the mass-to-volume ratio of lurasidone free base to the alcoholic solvent in the reaction system is 1:5 to 1:50 (W/V).

10. The method according to claim 1, wherein the mass-to-volume ratio of lurasidone free base to dichloromethane is 1:0.5 to 1:10 (W/V).

11. The method according to claim 9, wherein the mass-to-volume ratio of lurasidone free base to the alcoholic solvent in the reaction system is 1:8 to 1:15 (W/V).

12. The method according to claim 10, wherein the mass-to-volume ratio of lurasidone free base to dichloromethane is 1:1 to 1:4 (W/V).

* * * * *